(12) United States Patent
Kleyman et al.

(10) Patent No.: US 11,154,358 B1
(45) Date of Patent: Oct. 26, 2021

(54) ADJUSTABLE END EFFECTOR STRUCTURE FOR TISSUE ABLATION

(71) Applicants: Gennady I Kleyman, Brooklyn, NY (US); Annaniy Berensteyn, Edgewater, NJ (US)

(72) Inventors: Gennady I Kleyman, Brooklyn, NY (US); Annaniy Berensteyn, Edgewater, NJ (US)

(73) Assignee: Expandoheat, LLC, Atlantic Heights, NJ (US)

( * ) Notice: Subject to any disclaimer, the term of this patent is extended or adjusted under 35 U.S.C. 154(b) by 505 days.

(21) Appl. No.: 16/171,471

(22) Filed: Oct. 26, 2018

Related U.S. Application Data

(60) Provisional application No. 62/577,956, filed on Oct. 27, 2017.

(51) Int. Cl.
*A61B 18/18* (2006.01)
*A61B 18/00* (2006.01)

(52) U.S. Cl.
CPC .......... *A61B 18/1815* (2013.01); *A61B 2018/00041* (2013.01); *A61B 2018/00113* (2013.01); *A61B 2018/00136* (2013.01); *A61B 2018/00148* (2013.01); *A61B 2018/00559* (2013.01); *A61B 2018/00577* (2013.01); *A61B 2018/1861* (2013.01); *A61B 2018/1892* (2013.01)

(58) Field of Classification Search
CPC ...... A61B 18/1815; A61B 2018/00041; A61B 2018/00559; A61B 2018/1861; A61B 2018/00113; A61B 2018/00136; A61B 2018/00148; A61B 2018/00577; A61B 2018/1892

USPC .......................................................... 606/33
See application file for complete search history.

(56) References Cited

U.S. PATENT DOCUMENTS

| 5,057,106 A | * | 10/1991 | Kasevich | A61B 18/1815 |
| | | | | 606/33 |
| 6,610,055 B1 | * | 8/2003 | Swanson | A61B 18/1482 |
| | | | | 606/41 |
| 2006/0041254 A1 | * | 2/2006 | Francischelli | A61B 18/1445 |
| | | | | 606/41 |

(Continued)

OTHER PUBLICATIONS

Nolato Jabar LLC, Conductive Particle Filled Elastomers, 2004 (Year: 2004).*

(Continued)

*Primary Examiner* — Linda C Dvorak
*Assistant Examiner* — Nils A Potter

(57) ABSTRACT

An adjustable, structure providing an ablation apparatus, having a preformed structure made from compliant material such as rubber like material, foam or gel, with particles made of electromagnetic energy absorbing material. An antenna for radiating emitted microwave energy to generate heat and thus cause cavity ablation is located inside of the conformable adjustable structure. When end effector portion is inserted into the body cavity, the compliant adjustable structure is compliant to conform to a profile of the cavity to be ablated, and microwave energy is received to heat the adjustable structure resulting in heat energy that will ablate the cavity tissue in contact with the compliant end effector. Additionally, the shape of the end-effector compliant structure can be differently formed, depending of shape of tissue cavity to be ablated.

15 Claims, 2 Drawing Sheets

(56) References Cited

U.S. PATENT DOCUMENTS

2009/0182398 A1* 7/2009 Kleyman ............... A61B 18/18
607/98
2013/0256302 A1* 10/2013 Chu .................... H05B 6/6447
219/709

OTHER PUBLICATIONS

Northstar Polymers, NTG-9 Polyurethane Gel Elastomer with Less Tacky Surface, 2005 (Year: 2005).*
Stockwell Elastomerics, Open Cell Foam vs. Closed Cell Foam, 2014 (Year: 2014).*

* cited by examiner

ADJUSTABLE END EFFECTOR STRUCTURE FOR TISSUE ABLATION

BACKGROUND OF THE INVENTION

1. Field of the Invention

The invention relates to a device for tissue ablation, such as ablation of an artery, uterus and tissue cavity.

2. Description of Related Art

Conventional medical devices used for thermal ablation operate by applying heat, either directly or indirectly, for treatment of a biological tissue. Many conventional devices insert an inflatable balloon in a cavity within a patient's body and utilize a liquid to inflate the balloon after insertion. The liquid that expands the balloon remains in the balloon and is heated to operative temperature, maintained for a sufficient period of time to ablate of tissue. See, U.S. Pat. Nos. 5,843,144, 5,902,251, 6,041,260, 6,366,818 and 6,447,505, the contents of which are incorporated herein by reference.

U.S. Pat. No. 5,057,106 to Kasevich et al., the contents of which is incorporated herein by reference, describes a device having an active antenna located within the balloon to deliver microwave energy to the balloon wall or membrane constructed of a compliant material loaded with lossy particles, i.e. particles that dissipate electromagnetic energy, or coated with a flexible material with lossy particles to allow the balloon to directly absorb microwave energy.

A disadvantage of such balloon structure and other conventional devices is that the lossy materials, e.g. ferrite or graphite particles, are substantially rigid and adding particles of such lossy material to the balloon wall or to the coating of the balloon wall (made as a thin layer of particles of such lossy material) results in the balloon wall becoming substantially rigid and lacking necessary stretch ability and ability to comply with cavity profile which leads to a high risk to fail to ablate all cavity wall. Also, since the balloon wall or the coating of the balloon wall are very thin it is impossible to have in this thin structure sufficient quantity of microwave absorbing particles to completely absorb microwave energy and that causes substantial leakage of microwave energy, which results in uneven (excessive or insufficient) and unpredictable tissue heating. Yet another disadvantage of such balloon structure is that since its wall is made of substantially stretchable material, the distance between neighboring particles becomes large after the balloon is inflated, and, accordingly, the area density of the microwave absorbing particles become smaller which results I smaller amount of heat delivered by absorption of the microwave energy per unit of surface area of the ablated tissue.

Accordingly, conventional balloons and other inflatable treatment devices are unable to be heated fast, because they use a wire resistance heater and require a liquid circulation inside the balloon for efficient and homogeneous heating.

SUMMARY OF THE INVENTION

The present invention addresses at least the above-described problems and/or disadvantages and provides at least the advantages described below.

In a preferred embodiment, an adjustable, compliant end effector structure provided for an ablation apparatus, typically having a structure made from a compliant material such as rubber like material, foam or gel, with substantially evenly dispersed particles made of electromagnetic energy absorbing material. An antenna to emit microwave energy for cavity ablation, is located inside of adjustable structure and when end effector inserted into the body cavity, the compliant adjustable structure stretches to conform to a profile of the cavity to be ablated, and microwave energy will heat an adjustable structure of the electromagnetic energy absorbing material, which heat energy will ablate he body cavity tissue contacted with the compliant end effector. Additionally, shape of end-effector compliant structure can be different, depending of shape of tissue cavity to be ablated and can have a bulbous shape, cylindrical shape (e.g. for artery or vein ablation), spherical or can be customized depending of patient cavity profile.

BRIEF DESCRIPTION OF THE DRAWINGS

The above and other aspects, features and advantages of the present invention will become more apparent from the following detailed description when taken in conjunction with the accompanying drawing in which.

DETAILED DESCRIPTION OF THE PREFERRED EMBODIMENTS

Figure 1:
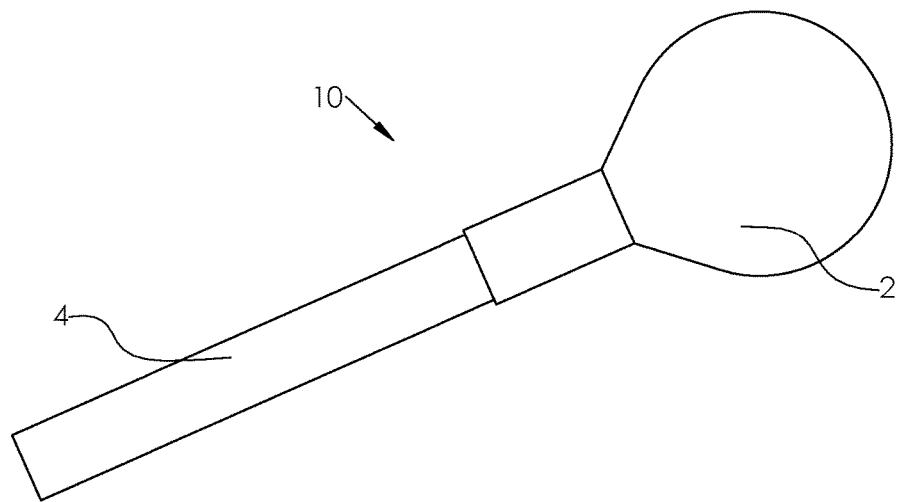
FIG. 1 illustrates an isometric view tissue-treating end effector of the present invention.

Various embodiments of the present invention are described in detail with reference to the accompanying drawings. Wherever possible, the same or similar reference numerals are used in the drawings and the description to refer to the same or like parts or steps. In the following description, specific details are provided to provide an overall understanding of embodiments of the present invention and those skilled in the art will recognize that various changes and modifications of the embodiments described herein can be made without departing from the scope and spirit of the invention. Descriptions of well-known functions and constructions are omitted for the sake of clarity and conciseness.

Figure 2:
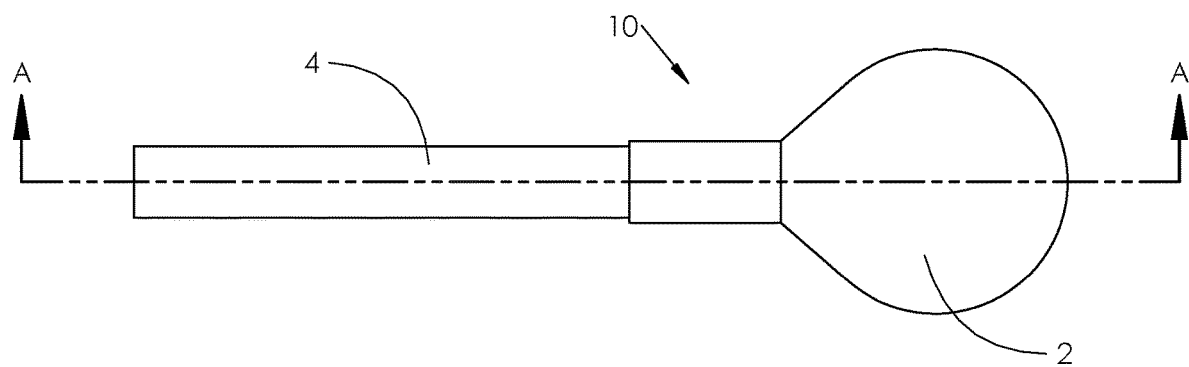
FIG. 2 illustrates a frontal view tissue-treating end effector of the present invention.

FIG. 1 and FIG. 2 is a view of one embodiment of an adjustable tissue-treating end effector 10 of the present invention, showing as a preferred embodiment a compliant structure 2 entirely filled with and made from microwave absorbing material, which is made of compliant and/or stretchable material such as rubber, gel and compliant foam. All of these with materials are impregnated with dispersed particles that can be made from nickel, silver, copper, silver-coated copper, silver-coated aluminum, silver-coated glass, nickel-coated graphite filled silicone, silver-coated aluminum or nickel-coated graphite or other conductive materials capable of absorbing microwave energy. Examples foam materials: ECCOSORB® high loss microwave absorbers available in foams manufactured by Laird Technologies. Examples of conductive particles filled elastomers: manufactured by Ja-Bar as example it can be material 802 where elastomer is silicone and filler is Ni/Gr. Similarly, the microwave absorbing materials can be made from gel (for example, non-tack polyurethane gel elastomer NTG-9 manufactured by Northstar Polymer) that can be filled with microwave absorbing particles. For the embodiment made with the microwave absorbing foam, the foam should preferably be of close cell type, and the elastomer material should be silicone base.

Figure 3:
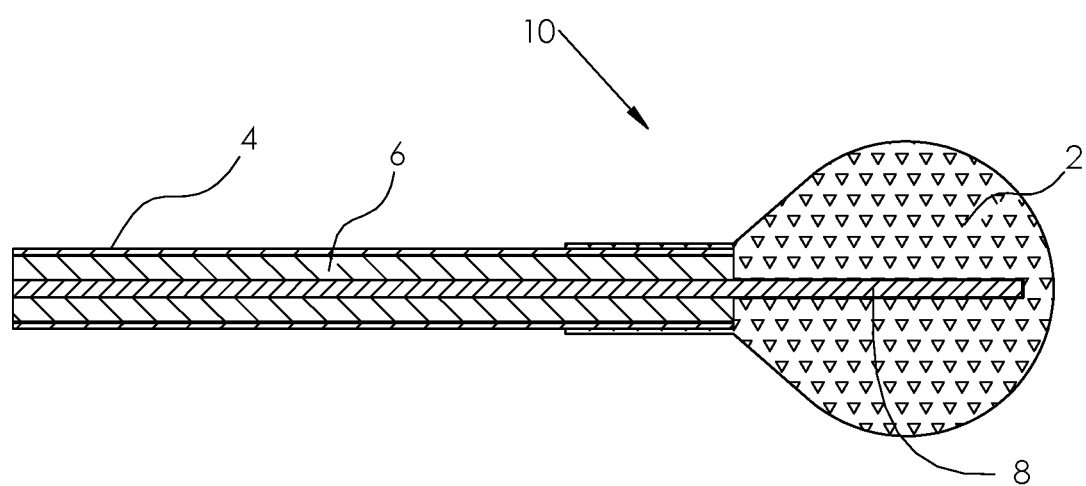
FIG. 3 shows a sectional view A-A according first embodiment of invention.

Compliant structure 2 according to one embodiment, is provided for insertion into a patient for ablation of an artery, a uterus or other cavity in biological tissue, and is attached to a cannula 4 or other device for penetration into a cavity of a patient. FIG. 3 is a cross sectional view A-A from FIG. 2 and it shows coaxial cable 4 for supplying microwave energy and antenna 8 that emits microwave energy, which is then absorbed by the microwave absorbing particles of compliant structure 2. This energy is then transferred into heat, which then ablates the contacted tissue when energy is applied from a microwave energy source, and the compliant structure 2 may be preformed to complement or adjust to a selected body cavity or organ shape to facilitate the desired tissue ablation.

Figure 4:
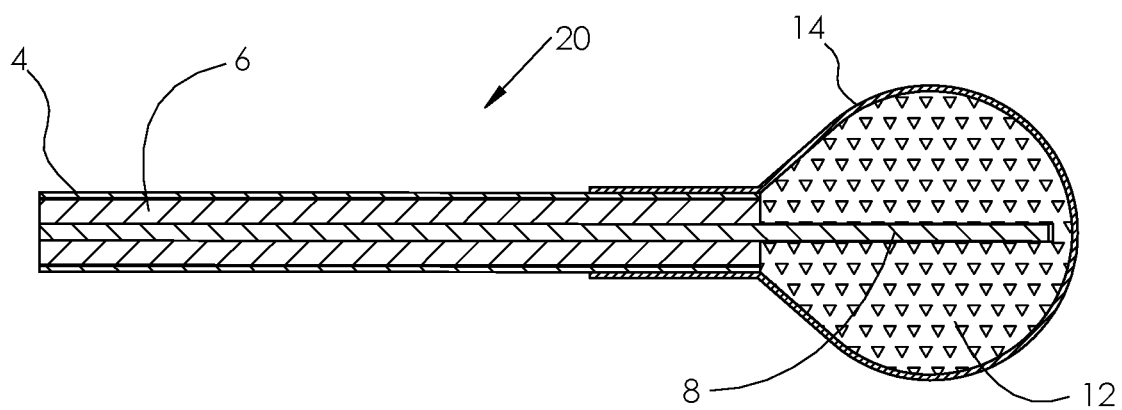
FIG. 4 shows a sectional view A-A according another embodiment of invention.

FIG. 4 is a cross sectional view A-A from FIG. 2 of another embodiment and it shows the coaxial cable 4 for supplying microwave energy from a microwave energy source, and antenna 8 (connected to a coaxial cable 4 conductor) that emits microwave energy, which is then absorbed by the microwave absorbing particles of compliant structure 12, made from microwave absorbing foam or microwave absorbing elastomer as described elsewhere, which is positioned inside an outer compliant structure 14, made from stretchable material, preferably silicone. For this embodiment microwave absorbing foam can be of close or open cell type. Compliant structure 14 made from silicone will reduce friction, because silicone has structure without pores and can be lubricated by many commonly used bio-compatible lubricants.

In all embodiments, the microwave absorbing medium such as the foam material, the elastomer and the gel, can be formed with the following microwave absorbing particles but not limited to them: silver (Ag) and glass fillers, glass fillers include regular glass formed as small beads, and fillers that include Nickel (Ni), copper (Cu), Aluminum (Al) used as a single filler or combined with other materials, for example combinations of Ag/Cu; Ag/Al; Ag/Ni; Ag/Glass.

By another embodiment, microwave absorbing foam, gel or elastomer (e.g. 12) can be inserted into the inside surface of a compliant resilient surface structure 14 or microwave absorbing end effector can be coated by compliant material, such as silicone, and in a further embodiment may entirely fill the compliant resilient structure 14. In this case, microwave-absorbing foam can be open or close cell.

Shape of heating end effector (member) can have a bulbous shape, cylindrical shape (for artery or vein ablation), spherical or can be customize depending of patient cavity profile. Microwave absorbing foam, gel or elastomer is a materials can be injection molded providing a shape of heating member different and customized for different surgical requirements.

While the invention has been shown and described with reference to an exemplary embodiment thereof, it will be understood by those skilled in the art that various changes in form and details may be made therein without departing from the spirit and scope of the invention.

What is claimed is:

1. An ablation apparatus, comprising:
an elongated member capable of providing microwave energy from a source to a first end; and
a heating member entirely filled with a microwave energy absorbing compliant resilient material and provide heat therefrom, and adjustable to conform to a profile of a cavity to be ablated and preformed in a selected shape having a surface emitting said heat in response to said microwave energy from said source first end, wherein said heating member comprises one of a bulbous shape and a spherical shape.

2. The ablation device of claim 1, further comprising an antenna connected to receive said microwave energy from said elongated member first end and to radiate said microwave energy, and being disposed within said heating member.

3. The ablation device of claim 1, wherein said selected shape corresponds to one of a type comprising a selected body cavity and an organ.

4. The ablation device of claim 1, wherein said compliant material includes particles made of electromagnetic energy absorbing material transferring absorbed said electromagnetic energy into heat output.

5. The ablation device of claim 4, wherein said compliant material comprises a silicone elastomer having a Ni/Gr filler.

6. The ablation device of claim 4, wherein said compliant material are impregnated with dispersed particles made from at least one of the group comprising nickel, silver, copper, silver-coated copper, silver-coated aluminum, silver-coated glass, nickel-coated graphite filled silicone, silver-coated aluminum and nickel-coated graphite.

7. The ablation device of claim 4, wherein said particles comprise at least one of the group energy microwave absorbing particles including silver (Ag) and glass fillers, including regular glass formed as small beads, and fillers that include Nickel (Ni), copper (Cu), Aluminum (Al).

8. The ablation device of claim 1, wherein said compliant material comprises at least one of the type comprising an elastomer material, a rubber-like material, a foam, and a gel.

9. The ablation device of claim 8, wherein said foam comprises a closed cell or open cell foam type, and said elastomer material comprises a silicone base elastomer.

10. The ablation device of claim 8, wherein said compliant material comprises a microwave absorbing material made from a non-tack polyurethane gel elastomer.

11. The ablation device of claim 1, wherein said heating member comprises a compliant one of a microwave absorbing foam and elastomer comprising a region entirely of a uniform cross-section.

12. The ablation device of claim 1, wherein said heating member comprises a compliant one of a microwave absorbing foam, gel and elastomer attached to the inside surface of a compliant resilient surface structure.

13. The ablation device of claim 1, wherein said elongated member comprises a cannula.

14. The ablation device of claim 1, wherein said elongated member comprises a coaxial cable.

15. The ablation device of claim 1, wherein said elongated member includes a coaxial cable having a conductor connected to an antenna disposed to radiate microwave energy within said heating member.

* * * * *